(12) United States Patent
Teamey et al.

(10) Patent No.: US 8,821,709 B2
(45) Date of Patent: *Sep. 2, 2014

(54) SYSTEM AND METHOD FOR OXIDIZING ORGANIC COMPOUNDS WHILE REDUCING CARBON DIOXIDE

(71) Applicant: Liquid Light, Inc., Monmouth Junction, NJ (US)

(72) Inventors: Kyle Teamey, Washington, DC (US); Jerry J. Kaczur, North Miami Beach, FL (US); Narayanappa Sivasankar, Plainsboro, NJ (US); Paul Majsztrik, Cranbury, NJ (US); Emily Barton Cole, Houston, TX (US); Andrew B. Bocarsly, Plainsboro, NJ (US)

(73) Assignee: Liquid Light, Inc., Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/724,082

(22) Filed: Dec. 21, 2012

(65) Prior Publication Data

US 2013/0118910 A1 May 16, 2013

Related U.S. Application Data

(60) Provisional application No. 61/703,238, filed on Sep. 19, 2012, provisional application No. 61/720,670, (Continued)

(51) Int. Cl.
*C25B 1/00* (2006.01)
*C25B 3/00* (2006.01)
(Continued)

(52) U.S. Cl.
CPC ............... *C25B 3/00* (2013.01); *C07C 29/149* (2013.01); *C25B 9/08* (2013.01); *C25B 3/02* (2013.01); *C07C 51/15* (2013.01); *C25B 15/08* (2013.01); *C25B 3/06* (2013.01); *C25B 3/04* (2013.01); *C07C 51/02* (2013.01); *C25B 1/00* (2013.01); *C25B 9/10* (2013.01)
USPC ........................... 205/413; 205/464; 205/555

(58) Field of Classification Search
USPC ......... 205/413, 440, 446, 448, 450, 455, 555, 205/464
See application file for complete search history.

(56) References Cited

U.S. PATENT DOCUMENTS

| 1,280,622 A | 10/1918 | Andrews |
| 3,019,256 A | 1/1962 | Dunn |

(Continued)

FOREIGN PATENT DOCUMENTS

| CA | 1146120 A1 | 5/1983 |
| CA | 1272161 A1 | 7/1990 |

(Continued)

OTHER PUBLICATIONS

Seshardi G., Lin C., Bocarsly A.B., A new homogeneous electrocatalyst for the reduction of carbon dioxide to methanol at low overpotential, Journal of Electroanalytical Chemistry, 1994, 372, pp. 145-150.

(Continued)

*Primary Examiner* — Edna Wong
(74) *Attorney, Agent, or Firm* — Suiter Swantz pc llo (57) ABSTRACT

Methods and systems for electrochemically generating an oxidation product and a reduction product may include one or more operations including, but not limited to: receiving a feed of at least one organic compound into an anolyte region of an electrochemical cell including an anode; at least partially oxidizing the at least one organic compound at the anode to generate at least carbon dioxide; receiving a feed including carbon dioxide into a catholyte region of the electrochemical cell including a cathode; and at least partially reducing carbon dioxide to generate a reduction product at the cathode.

8 Claims, 4 Drawing Sheets

Related U.S. Application Data filed on Oct. 31, 2012, provisional application No. 61/675,938, filed on Jul. 26, 2012, provisional application No. 61/703,229, filed on Sep. 19, 2012, provisional application No. 61/703,158, filed on Sep. 19, 2012, provisional application No. 61/703,175, filed on Sep. 19, 2012, provisional application No. 61/703,231, filed on Sep. 19, 2012, provisional application No. 61/703,232, filed on Sep. 19, 2012, provisional application No. 61/703,234, filed on Sep. 19, 2012, provisional application No. 61/703,187, filed on Sep. 19, 2012.

(51) Int. Cl.

| | | |
|---|---|---|
| *C07C 29/149* | (2006.01) | |
| *C25B 9/08* | (2006.01) | |
| *C25B 3/02* | (2006.01) | |
| *C07C 51/15* | (2006.01) | |
| *C25B 15/08* | (2006.01) | |
| *C25B 3/06* | (2006.01) | |
| *C25B 3/04* | (2006.01) | |
| *C07C 51/02* | (2006.01) | |
| *C25B 9/10* | (2006.01) | |

(56) References Cited

U.S. PATENT DOCUMENTS

| | | |
|---|---|---|
| 3,293,292 A | 12/1966 | Olivier et al. |
| 3,326,998 A | 6/1967 | Reusser et al. |
| 3,341,615 A | 9/1967 | Horst-Dieter Wulf et al. |
| 3,341,616 A | 9/1967 | Vives |
| 3,352,935 A | 11/1967 | Mahan |
| 3,361,653 A | 1/1968 | Miller |
| 3,401,100 A | 9/1968 | Macklin |
| 3,492,209 A | 1/1970 | Miller |
| 3,560,354 A | 2/1971 | Young |
| 3,607,962 A | 9/1971 | Krekeler et al. |
| 3,636,159 A | 1/1972 | Solomon |
| 3,720,591 A | 3/1973 | Skarlos |
| 3,745,180 A | 7/1973 | Rennie |
| 3,764,492 A | 10/1973 | Baizer et al. |
| 3,779,875 A | 12/1973 | Michelet |
| 3,894,059 A | 7/1975 | Selvaratnam |
| 3,959,094 A | 5/1976 | Steinberg |
| 4,072,583 A * | 2/1978 | Hallcher et al. ............ 205/423 |
| 4,087,470 A | 5/1978 | Suzuki |
| 4,088,682 A | 5/1978 | Jordan |
| 4,147,599 A | 4/1979 | O'Leary et al. |
| 4,162,948 A | 7/1979 | Yagii et al. |
| 4,219,392 A | 8/1980 | Halmann |
| 4,245,114 A | 1/1981 | Peltzman |
| 4,253,921 A | 3/1981 | Baldwin et al. |
| 4,256,550 A | 3/1981 | Niinobe et al. |
| 4,299,981 A | 11/1981 | Leonard |
| 4,343,690 A | 8/1982 | De Nora |
| 4,381,978 A | 5/1983 | Gratzel et al. |
| 4,421,613 A | 12/1983 | Goodridge et al. |
| 4,450,055 A | 5/1984 | Stafford |
| 4,476,003 A | 10/1984 | Frank et al. |
| 4,510,214 A | 4/1985 | Crouse et al. |
| 4,523,981 A | 6/1985 | Ang et al. |
| 4,545,886 A | 10/1985 | De Nora et al. |
| 4,547,271 A | 10/1985 | Bharucha et al. |
| 4,560,451 A | 12/1985 | Nielsen |
| 4,595,465 A | 6/1986 | Ang et al. |
| 4,608,132 A | 8/1986 | Sammells |
| 4,608,133 A | 8/1986 | Morduchowitz et al. |
| 4,619,743 A | 10/1986 | Cook |
| 4,661,422 A * | 4/1987 | Marianowski et al. ....... 429/476 |
| 4,673,473 A | 6/1987 | Ang et al. |
| 4,702,973 A | 10/1987 | Marianowski |
| 4,732,655 A | 3/1988 | Morduchowitz et al. |
| 4,756,807 A | 7/1988 | Meyer et al. |
| 4,845,252 A | 7/1989 | Schmidt et al. |
| 4,902,828 A | 2/1990 | Wickenhaeuser et al. |
| 4,968,393 A | 11/1990 | Mazur et al. |
| 5,074,974 A | 12/1991 | Toomey, Jr. |
| 5,107,040 A | 4/1992 | Repman et al. |
| 5,155,256 A | 10/1992 | Chapman |
| 5,198,086 A | 3/1993 | Chlanda et al. |
| 5,246,551 A | 9/1993 | Pletcher et al. |
| 5,290,404 A | 3/1994 | Toomey et al. |
| 5,294,319 A | 3/1994 | Kaczur et al. |
| 5,300,369 A | 4/1994 | Dietrich et al. |
| 5,412,150 A | 5/1995 | Wessel |
| 5,443,804 A | 8/1995 | Parker et al. |
| 5,474,658 A | 12/1995 | Scharbert et al. |
| 5,514,492 A | 5/1996 | Marincic et al. |
| 5,536,856 A | 7/1996 | Harrison et al. |
| 5,654,493 A | 8/1997 | Wessel |
| 5,804,045 A | 9/1998 | Orillon et al. |
| 6,001,500 A | 12/1999 | Bass et al. |
| 6,024,935 A | 2/2000 | Mills et al. |
| 6,137,005 A | 10/2000 | Honevik |
| 6,171,551 B1 | 1/2001 | Malchesky et al. |
| 6,251,256 B1 | 6/2001 | Blay et al. |
| 6,312,655 B1 | 11/2001 | Hesse et al. |
| 6,348,613 B2 | 2/2002 | Miyamoto et al. |
| 6,380,446 B1 | 4/2002 | Drew et al. |
| 6,465,699 B1 | 10/2002 | Grosso |
| 6,492,047 B1 | 12/2002 | Peled et al. |
| 6,777,571 B2 | 8/2004 | Chaturvedi et al. |
| 6,881,320 B1 | 4/2005 | Krafton et al. |
| 6,949,178 B2 | 9/2005 | Tennakoon et al. |
| 7,462,752 B2 | 12/2008 | Fong et al. |
| 7,883,610 B2 | 2/2011 | Monzyk et al. |
| 8,227,127 B2 | 7/2012 | Little et al. |
| 8,313,634 B2 | 11/2012 | Bocarsly et al. |
| 8,444,844 B1 | 5/2013 | Teamey et al. |
| 8,562,811 B2 | 10/2013 | Sivasankar et al. |
| 2001/0026884 A1 | 10/2001 | Appleby et al. |
| 2002/0022753 A1 | 2/2002 | Drew et al. |
| 2005/0139486 A1 | 6/2005 | Carson et al. |
| 2006/0102468 A1 | 5/2006 | Monzyk et al. |
| 2007/0004023 A1 | 1/2007 | Trachtenberg et al. |
| 2007/0012577 A1 | 1/2007 | Bulan et al. |
| 2007/0224479 A1 | 9/2007 | Tadokoro et al. |
| 2008/0223727 A1 | 9/2008 | Oloman et al. |
| 2008/0248350 A1 | 10/2008 | Little et al. |
| 2008/0283411 A1 | 11/2008 | Eastman et al. |
| 2008/0286643 A1 | 11/2008 | Iwasaki |
| 2008/0296146 A1 | 12/2008 | Toulhoat et al. |
| 2008/0314758 A1 | 12/2008 | Grosso |
| 2009/0014336 A1 | 1/2009 | Olah et al. |
| 2009/0030240 A1 | 1/2009 | Olah et al. |
| 2009/0057161 A1 | 3/2009 | Aulich et al. |
| 2009/0062110 A1 | 3/2009 | Koshino et al. |
| 2009/0308759 A1 | 12/2009 | Waycuilis |
| 2010/0069600 A1 | 3/2010 | Morelle et al. |
| 2010/0187123 A1 | 7/2010 | Bocarsly et al. |
| 2010/0187125 A1 | 7/2010 | Sandoval et al. |
| 2010/0191024 A1 | 7/2010 | Uenveren et al. |
| 2010/0196800 A1 | 8/2010 | Markoski et al. |
| 2010/0248042 A1 | 9/2010 | Nakagawa et al. |
| 2010/0270167 A1 | 10/2010 | McFarland |
| 2010/0282614 A1 | 11/2010 | Detournay et al. |
| 2010/0305629 A1 | 12/2010 | Lund et al. |
| 2010/0330435 A1 | 12/2010 | Nemeth et al. |
| 2011/0024288 A1 | 2/2011 | Bhavaraju et al. |
| 2011/0083968 A1 | 4/2011 | Gillliam et al. |
| 2011/0114501 A1 | 5/2011 | Teamey et al. |
| 2011/0114502 A1 | 5/2011 | Cole et al. |
| 2011/0114503 A1 | 5/2011 | Sivasankar et al. |
| 2011/0114504 A1 | 5/2011 | Sivasankar et al. |
| 2011/0143929 A1 | 6/2011 | Sato et al. |
| 2011/0186441 A1 | 8/2011 | LaFrancois et al. |
| 2011/0226632 A1 | 9/2011 | Cole et al. |
| 2011/0237830 A1 | 9/2011 | Masel |
| 2011/0318617 A1 | 12/2011 | Kirchev et al. |
| 2012/0004448 A1 | 1/2012 | Bhattacharyya et al. |
| 2012/0004449 A1 | 1/2012 | Bhattacharyya |

(56) References Cited

U.S. PATENT DOCUMENTS

| | | |
|---|---|---|
| 2012/0004454 A1 | 1/2012 | Bhattacharyya et al. |
| 2012/0018311 A1 | 1/2012 | Yotsuhashi et al. |
| 2012/0043301 A1 | 2/2012 | Arvin et al. |
| 2012/0132538 A1 | 5/2012 | Cole et al. |
| 2012/0199493 A1 | 8/2012 | Krafft et al. |
| 2012/0215034 A1 | 8/2012 | McFarland |
| 2012/0228147 A1 | 9/2012 | Sivasankar et al. |
| 2012/0277465 A1 | 11/2012 | Cole et al. |
| 2012/0292196 A1 | 11/2012 | Albrecht et al. |
| 2012/0295172 A1 | 11/2012 | Peled et al. |
| 2012/0298522 A1 | 11/2012 | Shipchandler et al. |
| 2012/0329657 A1 | 12/2012 | Eastman et al. |
| 2013/0062216 A1 | 3/2013 | Yotsuhashi et al. |
| 2013/0098772 A1 | 4/2013 | Bocarsly et al. |
| 2013/0105304 A1 | 5/2013 | Kaczur et al. |
| 2013/0105330 A1* | 5/2013 | Teamey et al. .............. 205/349 |
| 2013/0118907 A1 | 5/2013 | Deguchi et al. |
| 2013/0118911 A1* | 5/2013 | Sivasankar et al. ......... 205/455 |
| 2013/0134048 A1 | 5/2013 | Teamey et al. |
| 2013/0134049 A1 | 5/2013 | Teamey et al. |
| 2013/0140187 A1* | 6/2013 | Teamey et al. .............. 205/443 |
| 2013/0180863 A1 | 7/2013 | Kaczur et al. |
| 2013/0180865 A1 | 7/2013 | Cole et al. |
| 2013/0186771 A1 | 7/2013 | Zhai et al. |
| 2013/0199937 A1 | 8/2013 | Cole et al. |

FOREIGN PATENT DOCUMENTS

| | | |
|---|---|---|
| CA | 2043256 A1 | 12/1991 |
| CA | 2391938 A1 | 5/2001 |
| CN | 102190573 A | 9/2011 |
| DE | 1047765 A | 12/1958 |
| DE | 2301032 A | 7/1974 |
| EP | 0028430 A1 | 5/1981 |
| EP | 2329875 A1 | 6/2011 |
| FR | 853643 | 3/1940 |
| GB | 1096847 A | 12/1967 |
| GB | 1285209 A | 8/1972 |
| GB | 1584524 A | 4/1977 |
| GB | 2038335 A | 7/1980 |
| GB | 2312218 A | 10/1997 |
| JP | 64-015388 | 1/1989 |
| WO | 91/01947 A1 | 2/1991 |
| WO | WO 9724320 A1 | 7/1997 |
| WO | 9850974 A1 | 11/1998 |
| WO | WO 0015586 A1 | 3/2000 |
| WO | WO0138275 A1 | 5/2001 |
| WO | WO 200467673 A1 | 8/2004 |
| WO | 2007041872 A1 | 4/2007 |
| WO | WO 2007041872 A1 | 4/2007 |
| WO | 2007/091616 A1 | 8/2007 |
| WO | 2009108327 A1 | 9/2009 |
| WO | 2011116236 A2 | 9/2011 |
| WO | 2011160577 A1 | 12/2011 |
| WO | 2012015921 A1 | 2/2012 |
| WO | WO 2012046362 A1 | 4/2012 |
| WO | 2012166997 A2 | 12/2012 |

OTHER PUBLICATIONS

Eggins, Brown, McNeill, and Grimshaw, Carbon Dioxide Fixation by Electrochemical Reduction in Water to Oxalate and Glyoxylate, Tetrahedron Letters vol. 29, No. 8, pp. 945-948, 1988, Pergamon Journals Ltd., Printed in Great Britain.

M. Alvarez-Guerra et al., Conversion of carbon dioxide into formate using a continuous electrochemical reduction process in a lead cathode, Chem. Eng. J. (2012), http://dx.doi.org/10.1016/j.cej.2012.06.099.

Satoshi Kaneco, Kenji Iiba, Nobu-Hide Hiei, Kiyohisa Ohta, Takayuki Mizuno, and Tohru Suzuki, Electrochemical reduction of carbon dioxide to ethylene with high Faradaic efficiency at a Cu electrode in CsOH/methanol, Electrochimica Acta 44 (1999) 4701-4706.

Keith Scott, A Preliminary Investigation of the Simultaneous Anodic and Cathodic Production of Glyoxylic Acid, Electrochimica Acta, vol. 36, No. 9, pp. 1447-1452, 1991, Printed in Great Britain.

B. Eneau-Innocent et al., Electroreduction of carbon dioxide at a lead electrode in propylene carbonate: A spectroscopic study, Applied Catalysis B: Environmental 98 (2010) 65-71.

Kotaro Ogura et al., Selective Conversion of CO2 to Ethylene by the Electrolysis at a Three-Phase (Gas/Liquid/Solid) Interface in an Acidic Solution Containing Cupric Ions, Fuel Chemistry Division Preprints 2003, 48(1), 264.

S. Gambino and G. Silvestri, On the electrochemical reduction of carbon dioxide and ethylene, Tetrahedron Letters No. 32, pp. 3025-3028, 1973, Pergamon Press, Printed in Great Britain.

K.S. Udupa, G.S. Subramanian, and H.V.K. Udupa, The electrolytic reduction of carbon dioxide to formic acid, Electrochimica Acta, 1971, vol. 16, pp. 1593 to 1598, Pergamon Press, Printed in Northern Ireland.

Green et al., "Vapor-Liquid Equilibria of Formaldehyde-Methanol-Water", Industrial and Engineering Chemistry (Jan. 1955), vol. 47, No. 1, pp. 103-109.

Shibata et al., "Electrochemical Synthesis of Urea at Gas-Diffusion Electrodes Part VI. Simultaneous Reduction of Carbon Dioxide and Nitrite Ions with Various Metallophthalocyanine Catalysts". J. of Electroanalytical Chemistry (no month, 2001), vol. 507, pp. 177-184.

Jaaskelainen and Haukka, The Use of Carbon Dioxide in Ruthenium Carbonyl Catalyzed 1-hexene Hydroformylation Promoted by Alkali Metal and Alkaline Earth Salts, Applied Catalysis A: General, 247, 95-100 (2003).

Heldebrant et al., "Reversible Zwitterionic Liquids, The Reaction of Alkanol Guanidines, Alkanol Amidines, and Diamines wih CO2", Green Chem. (mo month, 2010), vol. 12, pp. 713-721.

Perez et al., "Activation of Carbon Dioxide by Bicyclic Amidines", J. Org. Chem. (no month, 2004), vol. 69, pp. 8005-8011.

Seshadri et al., A New Homogeneous Electrocatalyst for the Reduction of Carbon Dioxide to Methanol at Low Overpotential, Journal of Electroanalytical Chemistry, 372 (1994), 145-50.

Green et al., Vapor-Liquid Equilibria of Formaldehyde-Methanol-Water, Industrial and Engineering Chemistry (Jan. 1955), vol. 47, No. 1, pp. 103-109.

Scibioh et al., Electrochemical Reduction of Carbon Dioxide: A Status Report, Proc Indian Natn Sci Acad (May 2004), vol. 70, A, No. 3, pp. 407-462.

Gennaro et al., Homogeneous Electron Transfer Catalysis of the Electrochemical Reduction of Carbon Dioxide. Do Aromatic Anion Radicals React in an Outer-Sphere Manner?, J. Am. Chem. Soc. (no month, 1996), vol. 118, pp. 7190-7196.

Perez et al., Activation of Carbon Dioxide by Bicyclic Amidines, J. Org. Chem. (no month, 2004), vol. 69, pp. 8005-8011.

Zaragoza Dorwald, Side Reactions in Organic Synthesis, 2005, Wiley-VCH Verlag GmbH & Co. KGaA, Weinheim, Preface. p. IX.

Liansheng et al., Journal of South Central University Technology, Electrode Selection of Electrolysis with Membrane for Sodium Tungstate Solution, 1999, 6(2), pp. 107-110.

Mahmood et al., Use of Gas-Diffusion Electrodes for High-Rate Electrochemical Reduction of Carbon Dioxide. II. Reduction at Metal Phthalocyanine-Impregnated Electrodes, J. of Appl. Electrochem. (no month, 1987), vol. 17, pp. 1223-1227.

Tanno et al., Electrolysis of Iodine Solution in a New Sodium Bicarbonate-Iodine Hybrid Cycle, International Journal of Hydrogen Energy (no month, 1984), vol. 9, No. 10, pp. 841-848.

Seshadri et al., "A new homogeneous electrocatalyst for the reduction of carbon dioxide to methanol at low overpotential", Journal of Electroanalytical Chemistry and Interfacial Electro Chemistry, Elsevier, Amsterdam, NL, vol. 372, No. 1-2, Jul. 8, 1994, pp. 145-150.

Hossain et al., "Palladium and cobalt complexes of substituted quinoline, bipyridine and phenanthroline as catalysts for electrochemical reduction of carbon dioxide", Electrochimica Acta, Elsevier Science Publishers, vol. 42, No. 16, Jan. 1, 1997, pp. 2577-2585.

Fisher et al., "Electrocatalytic reduction of carbon dioxide by using macrocycles of nickel and cobalt", Journal of the American Chemical Society, vol. 102, No. 24, Sep. 1, 1980, pp. 7361-7363.

(56) References Cited

OTHER PUBLICATIONS

Ishida et al., Selective Formation of HC00—In the Electrochemical CO2 Reduction Catalyzed by URU(BPY)2(CO)2 3/4 2+ (BPY=2,2'-Bipyridine), Journal of the Chemical Society, Chemical Communications, Chemical Society, Letchworth, GB, Jan. 1, 1987, pp. 131-132.
Zhao et al., "Electrochemical reduction of supercritical carbon dioxide in ionic liquid 1-n-butyl-3-methylimidazolium hexafluorophosphate", Journal of Supercritical Fluids, PRA Press, US, vol. 32, No. 1-3, Dec. 1, 2004, pp. 287-291.
Scibioh et al, "Electrochemical Reductin of Carbon Dioxide: A Status Report," Proc. Indian Natn Science Acad., 70, A, No. 3, May 2004, pp. 407-762.
Fukaya et al., "Electrochemical Reduction of Carbon Dioxide to Formate Catalyzed by Rh(bpy)3CI3", Kagaku Gijutsu Kenkyusho Hokoku (no month, 1986), vol. 81, No. 5, pp. 255-258. 1-page abstract only.
Li et al., "The Electro-Reduction of Carbon Dioxide in a Continuous Reactor", J. of Applied Electrochemistry (no month, 2005), vol. 35, pp. 955-965.
Kaneco et al., "Electrochemical Reduction of Carbon Dioxide to Ethylene with High Faradaic Efficiency at a Cu Electrode in CsOH/Methanol", Electrochimica Acta (no month, 1999), vol. 44, pp. 4701-4706.
Yuan et al., "Electrochemical Activation of Carbon Dioxide for Synthesis of Dimethyl Carbonate in an Ionic Liquid", Electrochimica Acta (no month, 2009), vol. 54, pp. 2912-2915.
U.S. Appl. No. 13/724,647, filed Dec. 21, 2012; Office Action mailed Oct. 17, 2013.
U.S. Appl. No. 13/787,481, filed Mar. 6, 2013; Office Action mailed Sep. 13, 2013.
U.S. Appl. No. 13/724,082, filed Dec. 21, 2012; Office Action mailed Aug. 12, 2013.
U.S. Appl. No. 13/724,522, filed Dec. 21, 2012; Office Action mailed Oct. 1, 2013.
U.S. Appl. No. 13/724,885, filed Dec. 21, 2012; Office Action mailed Aug. 21, 2013.
U.S. Appl. No. 13/724,231, filed Dec. 21, 2012; Office Action mailed Aug. 20, 2013.
Hori et al, Chapter on "Electrochemical CO2 Reduction on Metal Electrodes," in the book "Modern Aspects of Electrochemistry," vol. 42, pp. 106 and 107.
Czerwinski et al, "Adsorption Study of CO2 on Reticulated vitreous carbon (RVC) covered with platinum," Analytical Letters, vol. 18, Issue 14 (1985), pp. 1717-1722.
Hammouche et al, Chemical Catalysis of Electrochemical Reactions. Homogeneous Catalysis of the Electrochemical Reduction of Carbon Dioxide by Iron ("0") Porphyrins. Role of the Addition of Magnesium Cations. J. Am. Chem. Soc. 1991, 113, 8455-8466.
Hossain et al., Palladium and Cobalt Complexes of Substituted Quinoline, Bipyridine and Phenanthroline as Catalysts for Electrochemical Reduction of Carbon Dioxide, Electrochimica Acta (no month, 1997), vol. 42, No. 16, pp. 2577-2785.
Scibioh et al., "Electrochemical Reduction of Carbon Dioxide: A Status Report", Proc Indian Natn Sci Acad (May 2004), vol. 70, A, No. 3, pp. 407-462.
Seshadri et al, "A new homogeneous catalyst for the reduction of carbon dioxide to methanol at low overpotential," Journal of Electroanalytical Chemistry, 372 (1994) 145-150.
Scibioh et al, "Electrochemical Reduction of Carbon Dioxide: A Status Report," Proc. Indian Natn Science Acad., 70, A, No. 3, May 2004, pp. 407-762.
Hori et al, "Enhanced Formation of Ethylene and Alcohols at Ambient Temperature and Pressure in Electrochemical Reduction of Carbon Dioxide at a Copper Electrode," J. Chem. Soc. Chem. Commun. (1988), pp. 17-19.
Hossain et al, "Palladium and Cobalt Complexes of Substituted Quinoline, Bipyridine and Phenanthroline as Catalysts for Electrochemical Reduction of Carbon Dioxide," Electrochimica Acta, vol. 42, No. 16 (1997), pp. 2577-2585.
Fischer, "Liquid Fuels from Water Gas", Industrial and Engineering Chemistry, vol. 17, No. 6, Jun. 1925, pp. 574-576.
Williamson et al, "Rate of Absorption and Equilibrium of Carbon Dioxide in Alkaline Solutions", Industrial and Engineering Chemistry, vol. 16, No. 11, Nov. 1924, pp. 1157-1161.
Hori, "Electrochemical CO2 Reduction on Metal Electrodes", Modern Aspects of Electrochemistry, No. 42, 2008, pp. 89-189.
Chen et al., "Tin oxide dependence of the CO2 reduction efficiency on tin electrodes and enhanced activity for tin/tin oxide thin-film catalysts." Journal of the American Chemical Society 134, No. 4 (2012): 1986-1989, Jan. 9, 2012, retrieved on-line.
Zhou et al. "Anodic passivation processes of indium in alkaline solution [J]" Journal of Chinese Society for Corrosion and Protection 1 (2005): 005, Feb. 2005.
Fukaya et al., "Electrochemical Reduction of Carbon Dioxide to Formate Catalyzed by Rh(bpy)3CI3", Kagaku Gijutsu Kenkyusho Hokoku (no month, 1986), vol. 81, No. 5, pp. 255-258.
James Grimshaw, Electrochemical Reactions and Mechanisms in Organic Chemistry, 2000, ISBN 978-0-444-72007-8. [retrieved on Jan. 3, 2014]. Retrieved from the Internet. <URL: http://f3.tiera.ru/ShiZ/Great%20Science%20TextBooks/Great%Science%20Textbooks%20DVD%20Library%202007%20-%20Supplement%20Five/Chemistry/Organic%20Chemistry/Electrochemical%20Reactions%20and%20Mechanisms%20in%20Organic%20Chemistry%20-%20J.%20Grimshaw%20%28Elsevier,%202000%29%WW.pdf>.
Fischer, J. et al. "The production of oxalic acid from CO2 and H2O." Journal of Applied Electrochemistry, 1981, vol. 11, pp. 743-750.
Goodridge, F. et al., The electrolytic reduction of carbon dioxide and monoxide for the production of carboxylic acids.: Journal of applied electrochemistry, 1984, vol. 14, pp. 791-796.
Kaneco et al., "Electrochemical Conversion of Carbon Dioxide to Formic Acid on Pb in KOH/Methanol Electrolyte at Ambient Temperature and Pressure", Energy (no month, 1998), vol. 23, No. 12, pp. 1107-1112.
Wu et al., "Electrochemical Reduction of Carbon Dioxide I. Effects of the Electrolyte on the Selectivity and Activity with Sn Electrode", Journal of the Electrochemical Society (no month, 2012), vol. 159, No. 7, pp. F353-F359.
Chaplin et al., "Effects of Process Conditions and Electrode Material on Reaction Pathways for Carbon Dioxide Electroreduction with Particular Reference to Formate Formation", Journal of Applied Electrochemistry (no month, 2003), vol. 33, pp. 1107-1123.
Jaime-Ferrer et al., "Three-Compartment Bipolar Membrane Electrodialysis for Splitting of Sodium Formate into Formic Acid and Sodium Hydroxide: Role of Diffusion of Molecular Acid", Journal of Membrane Science (no month, 2008), vol. 325, pp. 528-536.

\* cited by examiner

SYSTEM AND METHOD FOR OXIDIZING ORGANIC COMPOUNDS WHILE REDUCING CARBON DIOXIDE

CROSS-REFERENCE TO RELATED APPLICATIONS

The present application claims the benefit under 35 U.S.C. §119(e) of U.S. Provisional Application Ser. No. 61/720,670 filed Oct. 31, 2012, U.S. Provisional Application Ser. No. 61/703,238 filed Sep. 19, 2012 and U.S. Provisional Application Ser. No. 61/675,938 filed Jul. 26, 2012. Said U.S. Provisional Application Ser. No. 61/720,670 filed Oct. 31, 2012, U.S. Provisional Application Ser. No. 61/703,238 filed Sep. 19, 2012 and U.S. Provisional Application Ser. No. 61/675,938 filed Jul. 26, 2012 are incorporated by reference in their entireties.

The present application also claims the benefit under 35 U.S.C. §119(e) of U.S. Provisional Application Ser. No. 61/703,229 filed Sep. 19, 2012, U.S. Provisional Application Ser. No. 61/703,175 filed Sep. 19, 2012, U.S. Provisional Application Ser. No. 61/703,231 filed Sep. 19, 2012, U.S. Provisional Application Ser. No. 61/703,232, filed Sep. 19, 2012, U.S. Provisional Application Ser. No. 61/703,234 filed Sep. 19, 2012, U.S. Provisional Application Ser. No. 61/703,158 filed Sep. 19, 2012, U.S. Provisional Application Ser. No. 61/703,187 filed Sep. 19, 2012. The U.S. Provisional Application Ser. No. 61/703,229 filed Sep. 19, 2012, U.S. Provisional Application Ser. No. 61/703,175 filed Sep. 19, 2012, U.S. Provisional Application Ser. No. 61/703,231 filed Sep. 19, 2012, U.S. Provisional Application Ser. No. 61/703,232 filed Sep. 19, 2012, U.S. Provisional Application Ser. No. 61/703,234 filed Sep. 19, 2012, U.S. Provisional Application Ser. No. 61/703,158 filed Sep. 19, 2012 and U.S. Provisional Application Ser. No. 61/703,187 filed Sep. 19, 2012 are hereby incorporated by reference in their entireties.

CROSS REFERENCE TO RELATED APPLICATIONS

The present application incorporates by reference co-pending U.S. patent application Ser. No. 13/724,339 filed on Dec. 21, 2012, U.S. patent application Ser. No. 13/724,878 filed on Dec. 21, 2012, U.S. patent application Ser. No. 13/724,647 filed on Dec. 21, 2012, U.S. patent application Ser. No. 13/724,231 filed on Dec. 21, 2012, U.S. patent application Ser. No. 13/724,807 filed on Dec. 21, 2012, U.S. patent application Ser. No. 13/724,996 filed on Dec. 21, 2012, U.S. patent application Ser. No. 13/724,719filed on Dec. 21, 2012, and U.S. patent application Ser. No. 13/724,768 filed on Dec. 21, 2012, now U.S. Pat. No. 8,444,844 in their entireties.

TECHNICAL FIELD

The present disclosure generally relates to the field of electrochemical reactions, and more particularly to methods and/or systems for oxidizing organic compounds while reducing carbon dioxide.

BACKGROUND

The combustion of fossil fuels in activities such as electricity generation, transportation, and manufacturing produces billions of tons of carbon dioxide annually. Research since the 1970s indicates increasing concentrations of carbon dioxide in the atmosphere may be responsible for altering the Earth's climate, changing the pH of the ocean and other potentially damaging effects. Countries around the world, including the United States, are seeking ways to mitigate emissions of carbon dioxide.

A mechanism for mitigating emissions is to convert carbon dioxide into economically valuable materials such as fuels and industrial chemicals. If the carbon dioxide is converted using energy from renewable sources, both mitigation of carbon dioxide emissions and conversion of renewable energy into a chemical form that can be stored for later use will be possible.

SUMMARY OF THE PREFERRED EMBODIMENTS

Methods and systems for electrochemically generating an oxidation product and a reduction product may include one or more operations including, but not limited to: receiving a feed of at least one organic compound into an anolyte region of an electrochemical cell including an anode; at least partially oxidizing the at least one organic compound at the anode to generate at least carbon dioxide; receiving a feed including carbon dioxide into a catholyte region of the electrochemical cell including a cathode; and at least partially reducing carbon dioxide to generate a reduction product at the cathode.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

Referring generally to FIGS. 1-4, systems and methods of electrochemical co-production of products with a carbon-based reactant feed to an anode are disclosed. It is contemplated that the electrochemical co-production of products may include production of an oxidation product, such as an oxidized carbon-based product from an organic compound feed at the anode side of an electrochemical cell with co-production of a reduction product, such as reduction of carbon dioxide generated in the oxidation reaction to carbon-based products to include one, two, three, and four carbon chemicals at a cathode side of the electrochemical cell.

Before any embodiments of the disclosure are explained in detail, it is to be understood that the embodiments may not be limited in application per the details of the structure or the function as set forth in the following descriptions or illustrated in the figures. Different embodiments may be capable of being practiced or carried out in various ways. Also, it is to be understood that the phraseology and terminology used herein is for the purpose of description and should not be regarded as limiting. The use of terms such as "including," "comprising," or "having" and variations thereof herein are generally meant to encompass the item listed thereafter and equivalents thereof as well as additional items. Further, unless otherwise noted, technical terms may be used according to conventional usage. It is further contemplated that like reference numbers may describe similar components and the equivalents thereof.

The present invention encompasses oxidation or partial oxidation of an organic or carbon-containing compound at the anode of the electrochemical cell and an at least partially simultaneous reduction of carbon dioxide generated in the oxidation reaction to carbon-based products to include one, two, three, and four carbon chemicals at the cathode side of an electrochemical cell. If the anode is utilized for waste remediation, the organic compound may be oxidized to carbon dioxide and low toxicity products or partially oxidized to a compound which can be further oxidized by bacteria to carbon dioxide and water. The carbon dioxide may then be recycled into the cathode side of the electrochemical cell. If the anode is utilized for production of organic products, an organic compound may be partially oxidized to another valuable compound.

Figure 1:
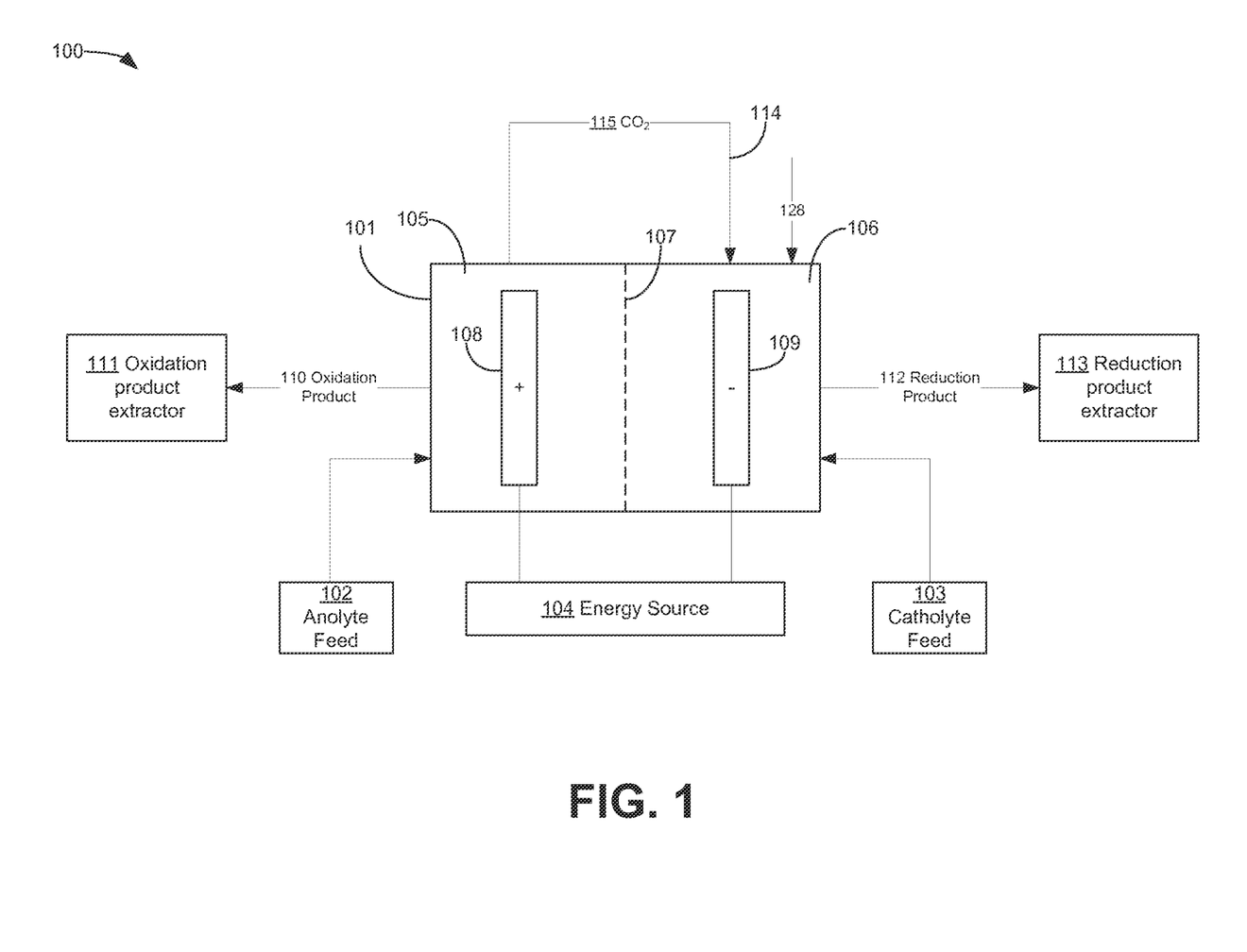
FIGS. 1-4 illustrate systems for electrochemically generating an oxidation product and a reduction product.

Referring to FIG. 1, a block diagram of a system 100 in accordance with an embodiment of the present disclosure is shown. The system 100 (or apparatus) generally includes an electrochemical cell 101 (also referred as a container, electrolyzer, or cell), an anolyte feed 102 including an organic compound, a catholyte feed 103 and an energy source 104.

The electrochemical cell 101 may be implemented as a divided cell. The divided cell may be a divided electrochemical cell and/or a divided photoelectrochemical cell. The electrochemical cell 101 may include an anolyte region 105 and a catholyte region 106 divided by separator 107. The anolyte region 105 may include an anode 108. The catholyte region 106 may include a cathode 109. The anolyte region 105 may include an anolyte which may include an anolyte feed 102 including an organic compound. The catholyte region 106 may include a catholyte feed 103 whereby carbon dioxide is dissolved in the catholyte. The energy source 104 may generate an electrical potential between the anode 108 and the cathode 109. The electrical potential may be a DC voltage. The energy source 104 may be configured to implement a variable voltage or constant current source.

In an embodiment of the invention the electrochemical cell 101 may produce valuable chemicals at the cathode 109 and remove or oxidize organic compounds from the anolyte feed 102 at the anode 108. The cathode 109 may be used to reduce carbon dioxide to carbon-containing chemicals. By using this process, the overall energy requirement for making the chemical at the cathode 109 and removing or oxidizing a contaminant at the anode 108 may be reduced by 50% or more. In addition, the oxidation product 110 generated from the organic compound may itself be a valuable product.

The electrochemical cell 101 may be operational to electrochemically produce an oxidation product 110 recoverable from the anolyte region 105 by an oxidation product extractor 111 while electrochemically reducing carbon dioxide in the catholyte region 106 to a reduction product 112 (e.g. a $C_1$ to $C_4$ reduction product) recoverable from the catholyte region 106 by a reduction product extractor 113.

The anode 108 reaction occurring in the anolyte region 105 may include a variety of partial and full oxidations of an organic contaminant in the anolyte feed 102 to the oxidation product 110. Oxidations may be direct, such as the conversion of ethane to ethanol at the anode. They also may be indirect, such as conversion of ethane to ethanol utilizing a halogenated compound produced at the anode. Examples are in Table 1 below:

TABLE 1

| Organic Compound in Anolyte Feed 102 | Oxidation Product(s) |
|---|---|
| A carboxylic acid such as formic acid | $CO_2$ |
| An aldehyde or ketone such as formaldehyde | A carboxylic acid such as formic acid or $CO_2$ |
| Alcohol such as ethanol | Acetic Acid, oxalic acid, $CO_2$ |
| A glycol such as ethylene glycol | Organic acids or $CO_2$ |
| An alkane such as dodecane | Organic acids or $CO_2$ |
| An unsaturated alkene organic chemical such as linoleic acid | Organic acids or $CO_2$ |
| An aromatic compound such as benzene or phenol | Organic acids or $CO_2$ |
| Cyanide | Cyanate, carbonate, $CO_2$, and nitrogen compounds |
| Surfactants such as lauryl sulfate | Organic acids, $CO_2$, or salts |
| A halogenated carbon compound such as chlorophenol | Dehalogenated organics, dehalogenated organic acids, or halide salts |
| Methane | Methanol, formaldehyde, formic acid |
| Ethane | Ethanol, Acetaldehyde, Acetic Acid |
| Ethylene | Ethylene oxide |
| Propane | Propylene, Propanol, propanoic acid, or other C3 chemicals |
| Propene | Propylene oxide, allyl alcohol |
| Butane | Butene, butadiene, butanol, or other C4 chemicals |
| Butene | Butadiene |
| Isobutane | Isobutylene, isobutyl alcohols |
| Ethylbenzene | Styrene |
| Ethyl acetate | Vinyl acetate |
| Methyl propionate, Ethyl propionate | Methyl acrylate, ethyl acrylate |
| Propionitrile | Acrylonitrile |
| Benzene | Phenol |
| Phenol | Hydroquinone, 1-2 dihydrobenzene (Catechol), 2,5 Cyclohexadiene-1-one, Benzoquinone, Maleic Acid, Oxalic Acid |

In an embodiment of the invention, CO2 115 and/or an oxidation product 110 may be produced during an oxidation reaction at the anode 108. The CO2 115 may be provided to the catholyte region 106 via a gas/fluid coupling 114. Additionally, a supplemental feed 128 including at least $CO_2$ may be provided to the catholyte region 106. The cathode 109 reaction occurring in the catholyte region 106 may then reduce the $CO_2$ 115 produced during the anode 108 reaction occurring in the anolyte region 105 and/or the supplemental feed 128 including at least $CO_2$ with the catholyte feed 103 to produce a reduction product 112 that may include one or more compounds. Examples of the reduction product 112 recoverable from the catholyte region 106 by reduction product extractor 113 may include carbon monoxide, formic acid, formaldehyde, methanol, oxalate, oxalic acid, glyoxylic acid, glycolic acid, glyoxal, glycolaldehyde, ethylene glycol, acetic acid, acetaldehyde, ethanol, lactic acid, propanoic acid, acetone, isopropanol, 1-propanol, 1,2-propylene glycol, 1-butanol, and/or 2-butanol.

In a specific embodiment, the oxidation reaction at the anode 108 may generate CO2 115 and an oxidation product 110 including acetic acid produced from oxidation of an anolyte feed 102 including waste phenol in the presence of water. The reduction product 112 may be acetic acid generated from a direct reduction of the co-generated CO2 115 at the cathode 109. The reaction at the anode 108 is $C_6H_5OH + 11H_2O \Rightarrow 6CO_2 + 28H^+ + 28e^-$. The reaction at the cathode 109 is $7CO_2 + 28H^+ + 28e^- \Rightarrow 3\frac{1}{2}CH_3COOH + 7H_2O$. The overall reaction for the electrochemical cell 101 is $C_6H_5OH + 4H_2O \Rightarrow 3\frac{1}{2}CH_3COOH$.

In other embodiments, the anode 108 may include electrocatalytic materials that have high oxygen overpotentials and thus help to preferentially oxidize organic compounds rather than water. Example materials include lead dioxide, tin oxides, electrically conductive titanium sub-oxides such as Ebonex ($Ti_4O_7$) with or without additional high oxidation overpotential electrocatalyst coatings, as well as boron doped diamond films on metal or electrically conductive substrates. If a partial oxidation is desired, this may be accomplished with a wide variety of precious metals and their oxides such as platinum, palladium, gold, ruthenium and iridium that are deposited on valve metal substrates such as titanium, niobium, and tantalum, in addition to transition metals and their oxides, other non-transition metal oxides, and stainless steels so long as the anode potential is less than that required for the oxidation of water and the anode material and/or coating electrocatalyst is stable in the particular organic anode oxidation reaction.

Figure 2:
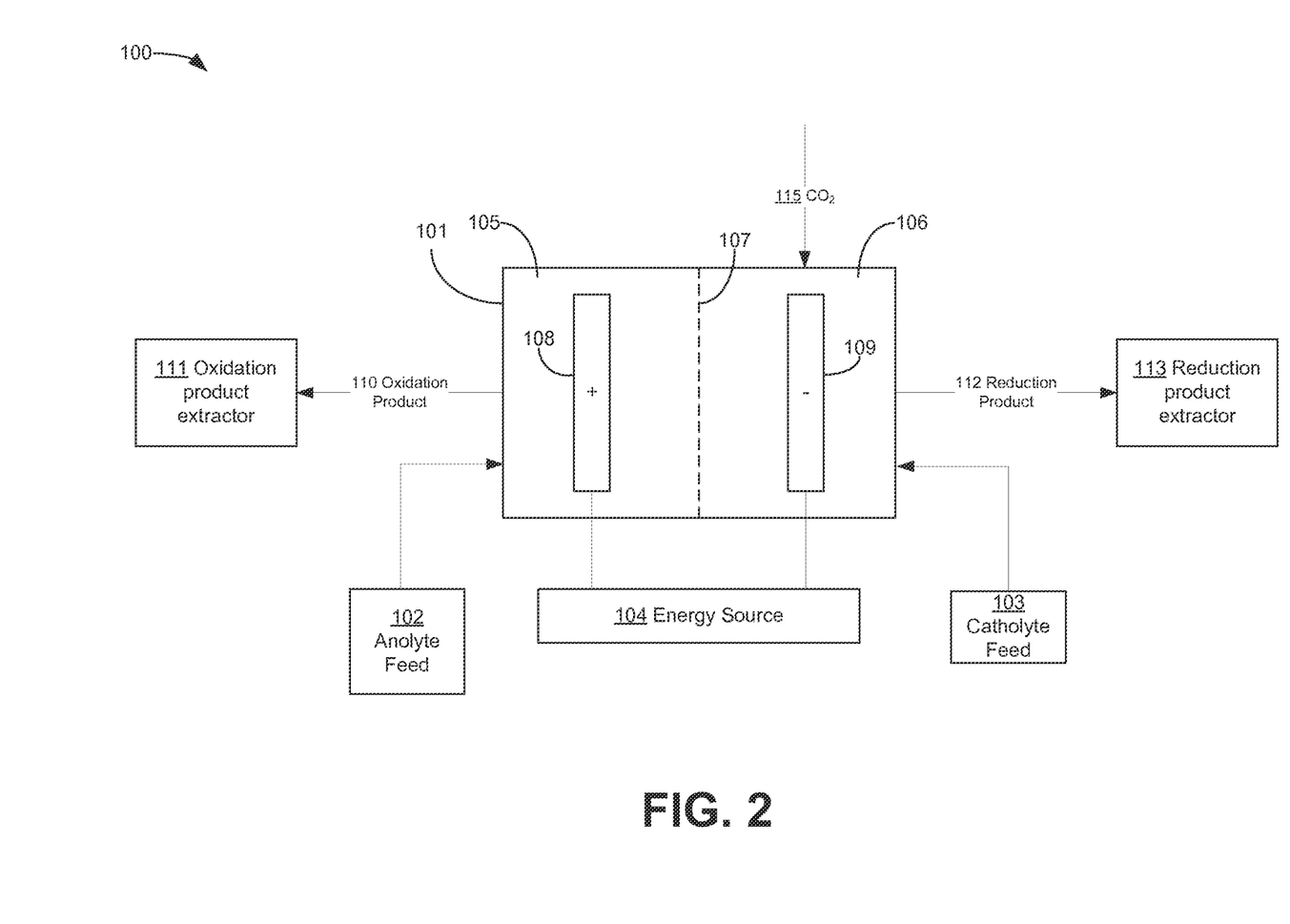

Referring to FIG. 2, in another embodiment, an anolyte feed 102 including an alkane or alcohol may be directly oxidized at the anode 108 to generate an oxidation product 110. Protons and electrons for reduction of CO2 115 may be provided to the cathode 109 while the oxidation product 110 is co-produced at the anode 108. The anolyte feed 102 including the alkane or alkene may be directly oxidized to an oxidation product 110 such as an alcohol or organic acid or oxide. In a specific embodiment, the anolyte feed 102 may include ethane which may be oxidized to an oxidation product 110 including ethanol. On the cathode 109 side, CO2 115 may be reacted on a high surface area cathode 109 to produce, for example, sodium acetate and byproduct hydrogen. A circulation pump may be used to provide mass transfer to obtain a high current Faradaic efficiency conversion to a reduction product 112 including acetate. The reduction product 112 may overflow the catholyte loop, and may later be converted (e.g. by the reduction product extractor 113) to an acetic acid form using an electrochemical acidification unit and concentrated by evaporation and/or distillation method. The overall reaction for the electrochemical cell 101 is $2CO_2 + 4C_2H_6 + 2H_2O \Rightarrow CH_3COOH + 4C_2H_5OH$.

The reaction occurring at the anode 108 may occur in gas phase, for instance in the case of gas phase reactants such as methane. The anode 108 reaction may also occur in liquid phase, such as the case of a an organic in solution. Preferably, the reaction at the anode 108 occurs in the gas phase and the anolyte region 105 includes water vapor. Reactions occurring at the cathode 109 may take place in a solvent selected from water, methanol, acetonitrile, propylene carbonate, ionic liquids, and/or other solvents in which CO2 115 is soluble.

The electrochemical cell 101 may be: 1) liquid phase at both the anode 108 in the anolyte region 105 and the cathode 109 in the catholyte region 106; 2) gas phase at the anode 108 in the anolyte region 105 where gas phase ethane and water vapor may be fed directly to the anode 108 and liquid phase at the cathode 109 in the catholyte region 106.

The electrochemical cell 101 may be operated at a current density of greater than 3 kA/m² (300 mA/cm²), or in suitable range of 0.5 to 5 kA/m² or higher. The operating voltage of the system at a current density of 1 kA/m² may be between 1.0-3.5 volts.

The anode 108, for example, may be a polymeric bound carbon current distributor anode including a carbon felt that is mechanically or chemically bonded to the current distributor with a specific surface area of at least 50 cm²/cm³ that is electrically connected to the current distributor and may fill a gap between a current distributor backplate of the cathode 109 and the separator 107, thus having a zero-gap anode 108.

Precious and transition metals and/or precious and transition metal oxide catalysts (e.g. a $RuO_2$ catalyst) may be added or incorporated into the structure of anode 108 in order to decrease anode potential and/or increase anode current density.

The cathode 109 may include high surface area materials such as copper, stainless steels, carbon, and silicon, which may be further coated with a layer of material which may be a conductive metal or semiconductor. There may be a very thin plastic screen against the cathode-side of the separator 107 to prevent the separator 107 from touching the high surface area cathode 109. The high surface area cathode 109 may be mechanically pressed against or bonded to a cathode current distributor backplate, which may be composed of material that has the same surface composition as the high surface area cathode. Preferred void volume for the cathode 109 may range from 30% to 98%. The surface area of the high surface area cathode 109 may be from 2 cm²/cm³ to 500 cm²/cm³ or higher. The surface area may also be defined as total area in comparison to a current distributor/conductor back plate, with a preferred range of 2× to 1000× or more. The actual total active surface area of the electrode structure is a function of the properties of the electrode catalyst deposited on the physical electrode structure which may be 2 to 1000 times higher in surface area than the physical electrode base structure.

For electrochemical reductions, the cathode electrode may be a suitable conductive electrode, such as Al, Au, Ag, Bi, C, Cd, Co, Cr, Cu, Cu alloys (e.g., brass and bronze), Ga, Hg, In, Mo, Nb, Ni, $NiCo_2O_4$, Ni alloys (e.g., Ni 625, NiHX), Ni—Fe alloys, Pb, Pd alloys (e.g., PdAg), Pt, Pt alloys (e.g., PtRh), Rh, Sn, Sn alloys (e.g., SnAg, SnPb, SnSb), Ti, V, W, Zn, stainless steel (SS) (e.g., SS 2205, SS 304, SS 316, SS 321), austenitic steel, ferritic steel, duplex steel, martensitic steel, Nichrome (e.g., NiCr 60:16 (with Fe)), elgiloy (e.g., Co—Ni—Cr), degenerately doped p-Si, degenerately doped p-Si:As, degenerately doped p-Si:B, degenerately doped n-Si, degenerately doped n-Si:As, and degenerately doped n-Si:B. Other conductive electrodes may be implemented to meet the criteria of a particular application. For photoelectrochemical reductions, the electrode may be a p-type semiconductor, such as p-GaAs, p-GaP, p-InN, p-InP, p-CdTe, $p-GaInP_2$ and p-Si, or an n-type semiconductor, such as n-GaAs, n-GaP, n-InN, n-InP, n-CdTe, $n-GaInP_2$ and n-Si. Other semiconductor electrodes may be implemented to meet the criteria of a particular application including, but not limited to, CoS, $MoS_2$, TiB, $WS_2$, SnS, $Ag_2S$, $CoP_2$, Fe3P, $Mn_3P_2$, MoP, $Ni_2Si$, $MoSi_2$, $WSi_2$, $CoSi_2$, $Ti_4O_7$, $SnO_2$, GaAs, GaSb, Ge, and CdSe.

Faradaic current efficiency of the anode 108 may be between 20 and 100%, and preferably greater than 25%, and the Faradaic current efficiency of the cathode 109 may be between 20 and 100% and preferably greater than 25%. The flow circulation of the anolyte and catholyte may be such that it provides sufficient flow for the reactions.

Operating the electrochemical cell at higher pressures (e.g. above atmospheric) may increase the current efficiency and allow operation of the electrochemical cell 101 at higher current densities.

The anolyte feed 102 may have a pH in a range of 1 to 14 depending on the organic compound in the anolyte feed 102 to be oxidized and the anode 108 to be used for the oxidation to achieve an optimum oxidation conversion efficiency of the organic compound in the anolyte feed 102 to CO2 115. The catholyte feed 103 may have a pH in a range from 3 to 12. The catholyte feed 103 pH may be a function of the catalysts used such that corrosion in the electrochemical cell 101 is limited.

Such catalysts may include, but are not limited to, pyridine, 2-picoline, and other aromatic heterocyclic amines.

A catholyte feed 103 electrolyte may be selected from alkali metal bicarbonates, carbonates, sulfates, and phosphates, borates, and/or hydroxides. More specifically, bromide salts, such as NaBr or KBr may be used. The electrolyte may include one or more of $Na_2SO_4$, KCl, $NaNO_3$, NaCl, NaF, $NaClO_4$, $KClO_4$, $K_2SiO_3$, $CaCl_2$, a guanidinium cation, a H cation, an alkali metal cation, an ammonium cation, an alkylammonium cation, a tetraalkyl ammonium cation, a halide anion, an alkyl amine, a borate, a carbonate, a guanidinium derivative, a nitrite, a nitrate, a phosphate, a polyphosphate, a perchlorate, a silicate, a sulfate, and a hydroxide.

A catholyte or an anolyte may comprise an aqueous solvent, a non-aqueous solvent, or a mixture of solvents containing one or more of water as well as protic or aprotic polar solvents such as methanol, ethanol, acetonitrile, propylene carbonate, ethylene carbonate, dimethyl carbonate, diethyl carbonate, dimethylsulfoxide, dimethylformamide, acetonitrile, acetone, tetrahydrofuran, N,N-dimethylacetaminde, dimethoxyethane, diethylene glycol dimethyl ester, butyrolnitrile, 1,2-difluorobenzene, γ-butyrolactone, N-methyl-2-pyrrolidone, sulfolane, 1,4-dioxane, nitrobenzene, nitromethane, acetic anhydride, and ionic liquids. An aqueous solvent comprises at least 5% water. A non-aqueous solvent comprises less than 5% water.

The catholyte may comprise a homogeneous catalyst. Homogeneous catalysts may comprise aromatic heterocyclic amines and may include, but are not limited to, unsubstituted and substituted pyridines and imidazoles. Substituted pyridines and imidazoles may include, but are not limited to mono and disubstituted pyridines and imidazoles. For example, suitable catalysts may include straight chain or branched chain lower alkyl (e.g., C1-C10) mono and disubstituted compounds such as 2-methylpyridine, 4-tertbutyl pyridine, 2,6 dimethylpyridine (2,6-lutidine); bipyridines, such as 4,4'-bipyridine; amino-substituted pyridines, such as 4-dimethylamino pyridine; and hydroxyl-substituted pyridines (e.g., 4-hydroxy-pyridine) and substituted or unsubstituted quinoline or isoquinolines. The catalysts may also suitably include substituted or unsubstituted dinitrogen heterocyclic amines, such as pyrazine, pyridazine and pyrimidine. Other catalysts generally include azoles, imidazoles, indoles, oxazoles, thiazoles, substituted species and complex multi-ring amines such as adenine, pterin, pteridine, benzimidazole, phenonthroline and the like.

Cross sectional area flow rates for the anolyte feed 102 and the catholyte feed 103 may be 2-3,000 gpm/ft$^2$ or more (0.0076-11.36 m$^3$/m$^2$) with a flow velocity range of 0.002 to 20 ft/sec (0.0006 to 6.1 m/sec).

Operating the catholyte region 106 at a higher relative operating pressure may allow more CO2 115 to dissolve in an aqueous catholyte feed 103. The electrochemical cell 101 may operate at pressures up to about 20 to 30 psig in a multi-cell stack design, although with modifications, the electrochemical cell 101 may operate at up to 100 psig. The anolyte region 105 would also need to be operated in a similar pressure range to minimize the pressure differential on the separator 107 separating the anolyte region 105 and the catholyte region 106. Special electrochemical designs may be required to operate electrochemical units at higher operating pressures up to about 60 to 100 atmospheres or greater, which is in the liquid $CO_2$ and supercritical $CO_2$ operating range.

In another example embodiment, a portion of a catholyte recycle stream may be separately pressurized using a flow restriction with backpressure or using a pump, with $CO_2$ injection, such that the pressurized stream may be injected into the catholyte region 106 of the electrochemical cell 101 thereby increasing the amount of dissolved $CO_2$ in the aqueous solution to improve the conversion yield.

The catholyte may be operated at a temperature range of −10 to 95° C., more preferably 5-60° C. The lower temperature will be limited by the catholytes used and their freezing points. In general, the lower the temperature, the higher the solubility of $CO_2$ in the aqueous solution phase of the catholyte, and would help in obtaining higher conversion and current efficiencies. The drawback is that the operating electrochemical cell voltages may be higher, so there is an optimization that would be done to produce the chemicals at the lowest operating cost. In addition, the catholyte may require cooling, so an external heat exchanger may be employed, flowing the catholyte through the heat exchanger and using cooling water to remove the heat and control the catholyte temperature.

The anolyte operating temperatures may be in the same ranges as the ranges for the catholyte, and may be in a range of 0° C. to 95° C. In addition, the anolyte may require cooling, so an external heat exchanger may be employed, flowing the anolyte through the heat exchanger and using cooling water to remove the heat and control the anolyte temperature.

The electrochemical cell 101 may be configured with zero-gap, flow-through with a recirculating catholyte feed 103 with various high surface area cathode 109 materials. More specifically, the electrochemical cell 101 may be configured with flooded co-current packed and/or trickle bed designs with the various high surface area cathode materials may be used. Further, bipolar stack electrochemical cell designs and high pressure cell designs may be employed The anode 108 may include an anode coating. The anode coating may include: precious metal oxides such as ruthenium and iridium oxides, as well as platinum and gold and their combinations as metals and oxides on valve metal substrates such as titanium, tantalum, vanadium, and/or or niobium. For other anolyte feeds 102 such as those operating in alkaline or hydroxide anolytes the anode material and anode coating may include: carbon, cobalt oxides, stainless steels, nickel and nickel alloys, other transition metals and their alloys and combinations which are stable as anodes.

Anodes may include electrocatalytic coatings applied to the surfaces of the base anode structure For example, for HBr, acid anolytes and oxidizing water generating oxygen, the preferred electrocatalytic coatings may include precious metal oxides such as ruthenium and iridium oxides, as well as platinum and gold and their combinations as metals and oxides on valve metal substrates such as titanium, tantalum, zirconium, or niobium. For bromine and iodine anode chemistry, carbon and graphite are particularly suitable for use as anodes. Polymeric bonded carbon materials may also be used. For other anolytes comprising alkaline or hydroxide electrolytes, anodes may include carbon, cobalt oxides, stainless steels, transition metals, and their alloys and combinations. High surface area anode structures that may be used which would help promote the reactions at the anode surfaces. The high surface area anode base material may be in a reticulated form composed of fibers, sintered powder, sintered screens, and the like, and may be sintered, welded, or mechanically connected to a current distributor back plate that is commonly used in bipolar cell assemblies. In addition, the high surface area reticulated anode structure may also contain areas where additional applied catalysts on and near the electrocatalytic active surfaces of the anode surface structure to enhance and promote reactions that may occur in the bulk solution away from the anode surface such as the reaction between bromine and the carbon based reactant being introduced into the anolyte. The anode structure may be gradated, so that the density of the may vary in the vertical or horizontal direction to allow the easier escape of gases from the anode structure. In this gradation, there may be a distribution of particles of materials mixed in the anode structure that may contain catalysts for bulk reactions.

The separator 107 may be configured as a cation ion exchange-type membrane. Specifically, the separator 107 may be configured to have a high rejection efficiency to anions and high rejection for alcohols. For example, the separator 107 may be a perfluorinated sulfonic acid based ion exchange membranes such as DuPont Nafion® brand unreinforced types N117 and N120 series or PTFE fiber reinforced N324 and N424 types, and similar related membranes manufactured the supplier trade names as Flemion®.

The separator 107 may be a multi-layer perfluorinated ion exchange membranes having a bilayer construction of a sulfonic acid based membrane layer bonded to a carboxylic acid based membrane layer, which efficiently operates with an anolyte and catholyte above a pH of about 2 or higher. For example, the separator 107 may be those sold by DuPont under their Nafion® trademark as the N900 series, such as the N90209, N966, N982, and the 2000 series, such as the N2010, N2020, and N2030 and all of their types and subtypes.

The separator 107 may be a hydrocarbon based membrane made from various cation ion exchange materials if the anion rejection is not as critical. For example, the separator 107 may be those sold by Sybron under their trade name Ionac®, AGC Engineering (Asahi Glass) under their Selemion® trade name, and Tokuyama Soda among others on the market.

The separator 107 may be a ceramic-based membrane. For example, the separator 107 may be a sodium super-ionic conductor (e.g. a "NASICON" having a composition $Na_{1+x}Zr_2Si_xP_{3-x}O_{12}$) which is chemically stable over a wide pH range for various chemicals and selectively transports sodium ions, and well as other ceramic based conductive membranes based on titanium oxides, zirconium oxides and yttrium oxides, and beta aluminum oxides. Preferably, the membrane or separator is chemically resistant to the anolyte and catholyte and operates at temperatures of less than 600 degrees C., and more preferably less than 500 degrees C.

The membrane may also include a thin layer of proton-conducting metal such as palladium, titanium, or vanadium to prevent crossover of ethanol while allowing conduction of protons to the cathode.

Figure 3:
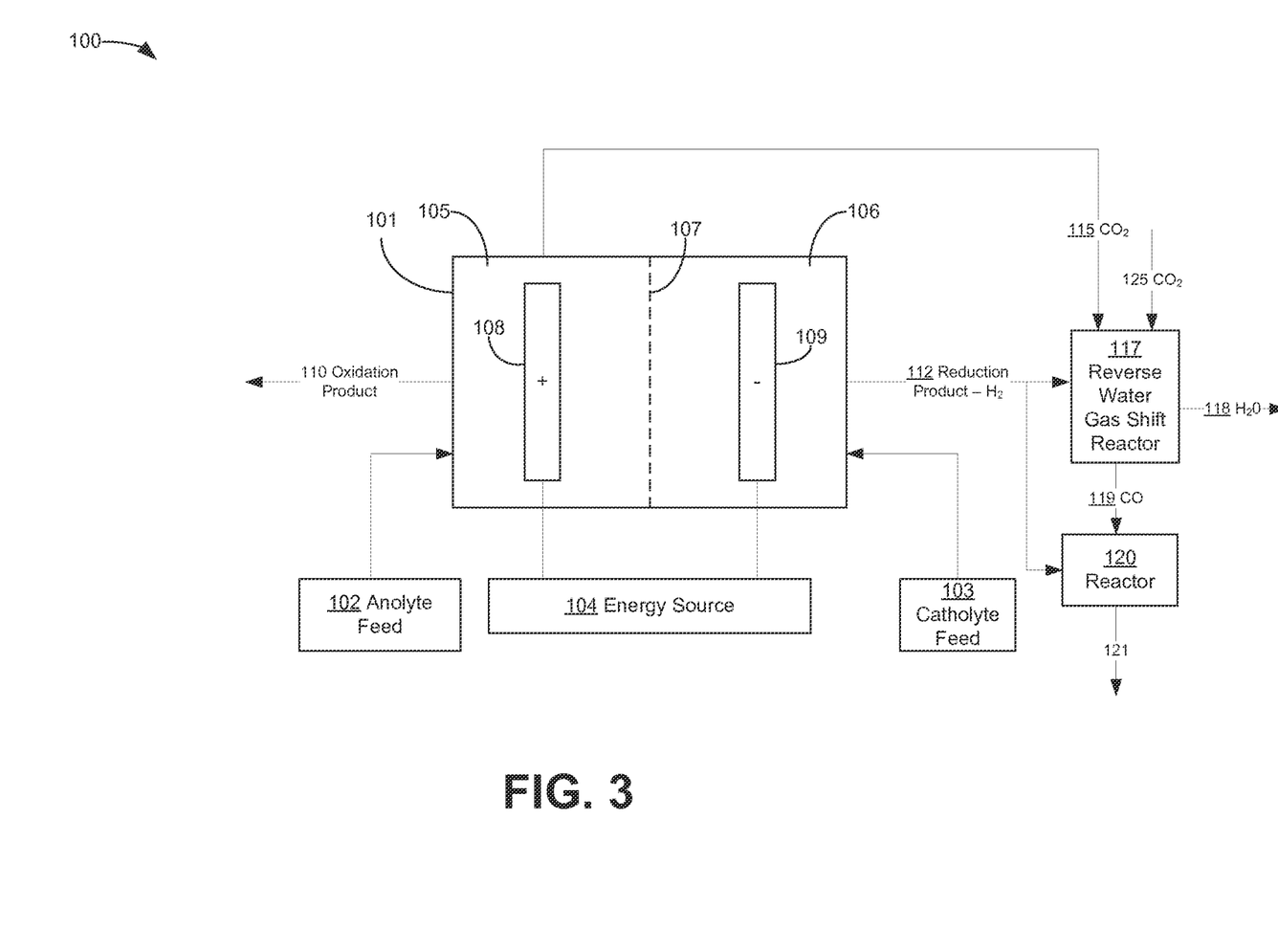

Referring to FIG. 3, the reaction at the cathode 109 in the catholyte region 106 may produce a reduction product 112 including $H_2$ which may combined with carbon dioxide. For example, CO2 115 cogenerated at the anode 108 (e.g. from oxidation of an alkane, alkene, phenol or aqueous solutions thereof) or, in a case where an oxidized organic product (e.g. ethanol, methanol, ethylene oxide, propylene oxide, etc.) is generated at the anode 108, an independent carbon dioxide feed 125, and the reduction product 112 including $H_2$ may be fed to a reverse water gas shift reactor 116 which may perform a reverse water gas shift reaction. This reverse water gas shift reaction performed by reverse water gas shift reactor 116 may produce water 117 and carbon monoxide 118. The carbon monoxide 118 along with the reduction product 112 including $H_2$ may be combined at reactor 119. The reactor 119 may cause a reaction, such as a Fischer-Tropsch synthesis reaction, to reduce carbon monoxide to a product 120 including one or more of methane, methanol, hydrocarbons, glycols and/or olefins by utilizing the $H_2$ reduction product 112 from the reaction at the cathode 109 in the catholyte region 106.

Figure 4:
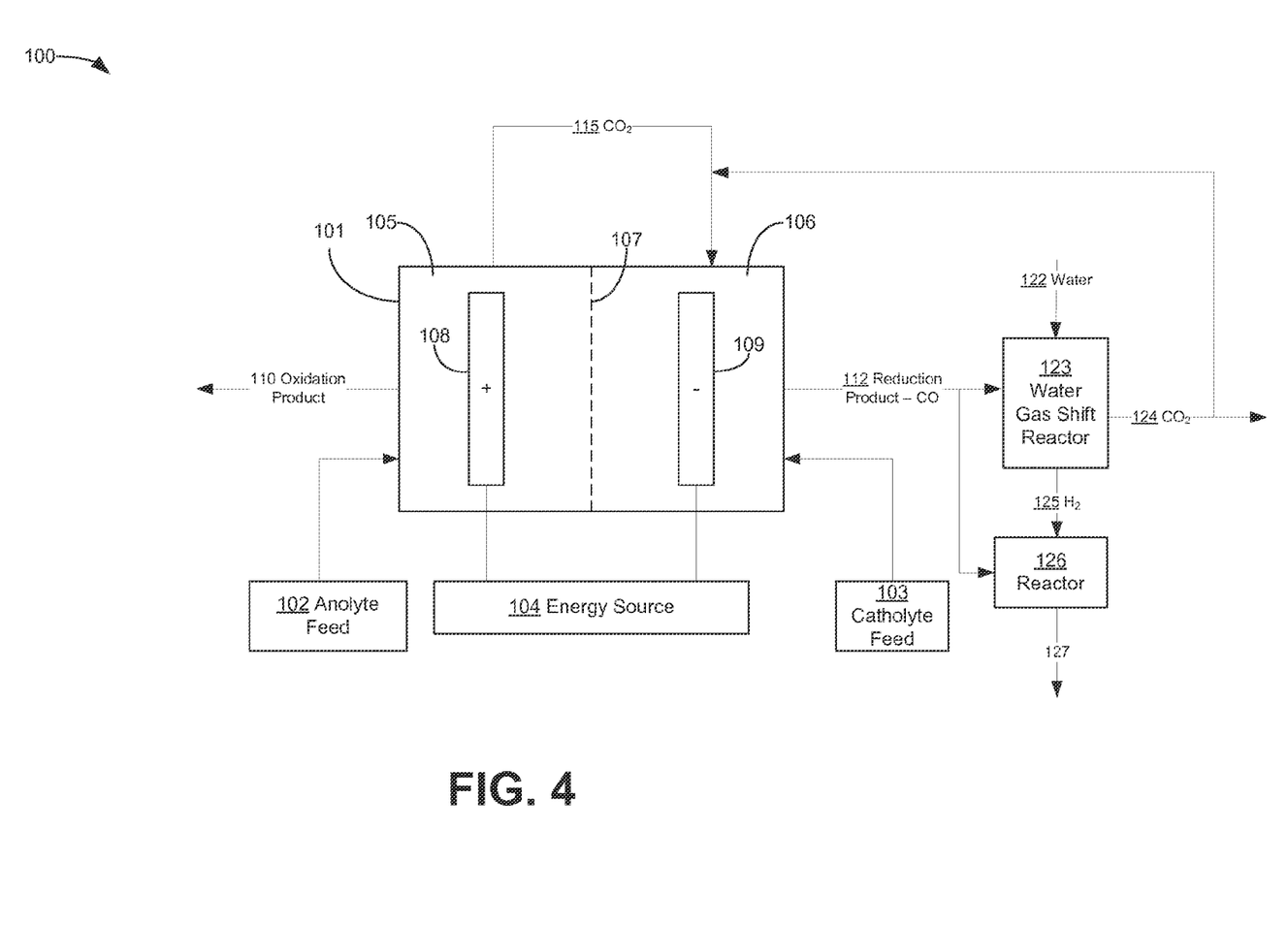

Referring to FIG. 4, the reaction at the cathode 109 in the catholyte region 106 may produce reduction product 112 including carbon monoxide may be combined with water 121 in a water gas shift reactor 122 which may perform a water gas shift reaction. This water gas shift reaction performed by reactor 122 may produce $CO_2$ 123 and $H_2$ 124. The reduction product 112 including carbon monoxide and H2 124 may be combined at a reactor 125. The reactor 125 may cause a reaction, such as a Fischer-Tropsch synthesis reaction, to reduce carbon monoxide to one or more products 126 such as methane, methanol, hydrocarbons, glycols, olefins by utilizing H2 124. The CO2 123 produced by the water gas shift reaction of reactor 122 may be recycled as an input feed to the catholyte region 106. In a case where CO2 115 is cogenerated at the anode 108 and fed to the catholyte region 106, the CO2 123 may be combined with the CO2 115.

The rate of the generation of reactant formed in the anolyte region from the anode reaction, such as the oxidation of an alkane to a carboxylic acid, is contemplated to be proportional to the applied current to the electrochemical cell. The rate of the input or feed of the carbon based reactant, for example ethane, into the anolyte region should then be fed in proportion to the generated anode reactant. The molar ratio of the carbon based reactant to the generated anode reactant may be in the range of 100:1 to 1:10, and more preferably in the range of 50:1 to 1:5.

Similarly, the rate of the generation of the formed electrochemical carbon dioxide reduction product in the catholyte region, such as CO, is contemplated to be proportional to the applied current to the electrochemical cell. The rate of the input or feed of carbon dioxide into the catholyte region should be fed in a proportion to the applied current. The cathode reaction efficiency would determine the maximum theoretical formation in moles of the carbon dioxide reduction product. It is contemplated that the ratio of carbon dioxide feed to the theoretical moles of potentially formed carbon dioxide reduction product would be in a range of 100:1 to 2:1, and preferably in the range of 50:1 to 5:1, where the carbon dioxide is in excess of the theoretical required for the cathode reaction. The carbon dioxide excess would then be recycled back to the catholyte region.

The molar ratio of the carbon based reactant to the generated anode reactant may be in the range of 100:1 to 1:10, and more preferably in the range of 50:1 to 1:5. The anolyte product output in this range can be such that the output stream contains little or no free bromine in the product output to the second product extractor, or it may contain unreacted bromine. The operation of the extractor and its selected separation method, may use for example, fractional distillation, to separate the actual oxidation products.

In the present disclosure, the methods disclosed may be implemented as sets of instructions or software readable by a device. Further, it is understood that the specific order or hierarchy of steps in the methods disclosed are examples of exemplary approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages.

The form described is merely explanatory, and it is the intention of the following claims to encompass and include such changes.

What is claimed is:

1. A method for at least partially simultaneously electrochemically generating carbon dioxide and a reduction product, the method comprising:
   receiving a feed of at least one organic compound into an anolyte region of an electrochemical cell including an anode, the feed of at least one organic compound includes an aqueous solution of the organic compound, the at least one organic compound is selected from the group consisting of an alkane, an alkene, an aromatic, a carboxylic acid, an aldehyde, a ketone, an alcohol, a phenol, a sugar, a glycol, and a halogenated organic compound;
   receiving a feed including carbon dioxide into a catholyte region of the electrochemical cell including a cathode; and
   applying an electrical potential between the anode and the cathode sufficient for at least partially oxidizing the at least one organic compound at the anode to generate at least carbon dioxide and at least partially reducing carbon dioxide at the cathode to generate a reduction product, wherein the feed including carbon dioxide includes at least one of a feed including the carbon dioxide generated at the anode and a supplemental feed including carbon dioxide.

2. The method of claim 1, wherein the anode includes an electrocatalyst including at least one of lead dioxide, tin oxides, conductive titanium sub-oxides or boron doped diamond.

3. A method for at least partially simultaneously electrochemically generating carbon dioxide and a reduction product, the method comprising:
   receiving a feed of at least one organic compound into an anolyte region of an electrochemical cell including an anode, the at least one organic compound is selected from the group consisting of an alkane, an alkene, an aromatic, a carboxylic acid, an aldehyde, a ketone, an alcohol, a phenol, a sugar, a glycol, and a halogenated organic compound;
   receiving a feed including carbon dioxide into a catholyte region of the electrochemical cell including a cathode; and
   applying an electrical potential between the anode and the cathode sufficient for at least partially oxidizing the at least one organic compound at the anode to generate at least carbon dioxide and at least partially reducing carbon dioxide at the cathode to generate a reduction product, wherein the feed of at least one organic compound includes an aqueous solution of the organic compound.

4. The method of claim 1, wherein the feed including carbon dioxide includes at least one of a feed including the carbon dioxide generated at the anode and a supplemental feed including carbon dioxide.

5. The method of claim 3, wherein the anode includes an electrocatalyst including at least one of lead dioxide, tin oxides, conductive titanium sub-oxides or boron doped diamond.

6. A method for at least partially simultaneously electrochemically generating carbon dioxide and a reduction product, the method comprising:
   receiving a feed of at least one organic compound into an anolyte region of an electrochemical cell including an anode, the at least one organic compound is selected from the group consisting of an alkane, an alkene, an aromatic, a carboxylic acid, an aldehyde, a ketone, an alcohol, a phenol, a sugar, a glycol, and a halogenated organic compound;
   receiving a feed including carbon dioxide into a catholyte region of the electrochemical cell including a cathode; and
   applying an electrical potential between the anode and the cathode sufficient for at least partially oxidizing the at least one organic compound at the anode to generate at least carbon dioxide and at least partially reducing carbon dioxide at the cathode to generate a reduction product, wherein the anode includes an electrocatalyst including at least one of lead dioxide, tin oxides, conductive titanium sub-oxides and boron doped diamond.

7. The method of claim 6, wherein the feed including carbon dioxide includes at least one of a feed including the carbon dioxide generated at the anode and a supplemental feed including carbon dioxide.

8. The method of claim 6, wherein the feed of at least one organic compound includes an aqueous solution of the organic compound.

* * * * *